United States Patent [19]

Hallam

[11] Patent Number: 4,904,639

[45] Date of Patent: Feb. 27, 1990

[54] AIR FRESHENERS

[75] Inventor: Wilfred H. Hallam, Broxton, England

[73] Assignee: Joseph Burley, New Brighton, Wales

[21] Appl. No.: 245,976

[22] Filed: Sep. 19, 1988

Related U.S. Application Data

[63] Continuation of Ser. No. 914,793, Oct. 2, 1986, abandoned.

[30] Foreign Application Priority Data

Oct. 2, 1985 [GB] United Kingdom ............... 8524228

[51] Int. Cl.$^4$ .............................................. A61K 7/46
[52] U.S. Cl. ........................................ 512/4; 424/76.4
[58] Field of Search ........................... 512/4; 424/76.4

[56] References Cited

U.S. PATENT DOCUMENTS

| | | | |
|---|---|---|---|
| 2,691,615 | 10/1954 | Turner et al. | 424/76 |
| 2,927,055 | 3/1960 | Lanzet | 424/76 |
| 3,310,472 | 3/1967 | Kohl | 512/4 |
| 3,576,760 | 4/1971 | Gould et al. | 424/76 |
| 3,685,734 | 8/1972 | Paciorek et al. | 239/56 |
| 3,688,985 | 9/1972 | Engel | 289/54 |
| 3,767,787 | 10/1973 | Segal | 424/76 |
| 3,780,195 | 12/1973 | Balassa | 512/4 |
| 3,944,662 | 3/1976 | Miller, Jr. et al. | 428/78 |
| 3,945,950 | 3/1976 | Vosganiantz | 252/522 A |
| 4,155,742 | 5/1979 | Sakurai et al. | 424/76 |
| 4,587,129 | 5/1986 | Kliment | 424/76 |

FOREIGN PATENT DOCUMENTS

| | | | |
|---|---|---|---|
| 152982 | 8/1985 | European Pat. Off. | 512/4 |
| 55-81655 | 6/1980 | Japan | 512/4 |
| 58-1457 | 1/1983 | Japan | 424/76 |
| 60-260509 | 12/1985 | Japan | 512/2 |
| 2164853 | 4/1986 | United Kingdom | 512/4 |

OTHER PUBLICATIONS

Miyake, Chem. Abst., vol. 73, #123441j (1970).

Primary Examiner—James H. Reamer
Attorney, Agent, or Firm—Fleit, Jacobson, Cohn, Price, Holman & Stern

[57] ABSTRACT

The present specification discloses an air freshener and a method of manufacturing the air freshener. The air freshener comprises a homogenized mixture of a water-miscible solid thermoplastic synthetic plastics material and water, with a perfume incorporated therein and therethrough. A suitable plastics material is a polyethylene glycol. The air freshener is manufactured by mixing the thermoplastic synthetic plastics material in granular or particulate form with a plasticizer therefore, homogenizing the mixture and incorporating a quantity of perfume in the homogenized mixture. In use, additional perfume can be released as desired by adding water to the air freshener.

3 Claims, No Drawings

AIR FRESHENERS

This application is a continuation of application Ser. No. 914,793, filed Oct. 2, 1986.

DESCRIPTION

The present invention relates to a method of manufacturing an air freshener and the air freshener produced by said method.

Certain known air fresheners comprise a block of material which holds a quantity of perfume. The material is air permeable so that air can enter the block and the perfume can thus evaporate into the air and leave the block, to thus scent the surrounding atmosphere. Certain such known air fresheners use a wax material to hold the perfume. However, this wax material has a low air permeability, i.e. a relatively small intersticial molecular spacing, and thus the perfume is released slowly over a long period of time. Further, with this low air permeability property, whilst the air permeates into the surface layer of the block of material to release the perfume in the surface layer, it becomes more difficult and therefore less efficient to release the perfume from the inner regions of the block. This is especially the case where the block of material is located in a container with only part of its surface area exposed to the ambient atmosphere. In such a case, the rate of perfume release becomes less and less as time goes on, so that even though perfume remains in the block of material, its rate of release is totally inadequate and the air freshener has to be thrown away.

Besides having the problem outlined hereabove, air fresheners made using a wax material are relatively expensive to manufacture, as large amounts of heat are required to melt the wax material and allow the perfume to be added, the wax material being subsequently set in moulds to provide desired shapes of air freshener. To counter the problem of low air permeability as described hereabove, the wax material is sometimes set in a thin layer, e.g. as a sheet or as a hollow shape. However, this limits the amount of perfume to be contained in a particular size of air freshener.

The aim of the present invention is to provide a simple and relatively inexpensive air freshener which is more efficient in its release of perfume than prior art air fresheners of a similar type.

According to the present invention there is provided an air freshener which comprises a solid plasticised thermoplastic synthetic plastics material having perfume incorporated therein and therethrough.

The present invention also provides a method of manufacturing an air freshener comprising mixing a thermoplastic synthetic plastics particulate or granular material with a plasticiser therefor, homogenising the mixture and incorporating a quantity of perfume therein. The homogenising of the mixture may be effected in any convenient manner such as by heating and stirring.

In a preferred embodiment of the present invention granular polyethylene glycol is mixed with water to produce a fluid mass. Another suitable plasticiser other than water, may be alternatively used, if desired. This fluid mass is then heated slightly, the heat homogenising the mass, and liquid perfume is added. The resultant mass is then allowed to solidify either in moulds to produce desired shapes, or in aesthetic permanent containers.

Clearly the method of the present invention is simpler and less expensive than the prior art production wherein large amounts of expensive heat are required to initially melt the wax material; this being in comparison to the addition of a plasticiser, e.g. water, in the present invention and the subsequent application of a relatively small amount of heat to homogenise the fluid mass.

Further, in comparison with the prior art wax block production up to three times more perfume can be incorporated per unit volume of the air freshener by the method of the present invention. It has also been found that in addition to a higher concentration of perfume in the air freshener, the air freshener of the present invention has a longer life in comparison with prior art air fresheners.

It is believed that the relatively large molecular structure of the synthetic plastics material provides relatively large intersticial spaces which result in good air permeability and thus the efficient operation of the air freshener.

When the synthetic plastics material is water miscible such as polyethylene glycol, a user may intermittently apply a layer of water to the surface of the air freshener block to liquefy the surface layer of the block. Because most perfumes are hydrophobic, the perfume separates into a separate oil phase which floats on the surface of the water and evaporates more quickly than usual. Thus, when a water-miscible synthetic plastics material is used by simply adding a small quantity of water, the performance of the air freshener of the present invention can be boosted at any required point in time.

EXAMPLE 45 grams of granular Polyethylene Glycol 12000 is mixed with 15 mls of water to produce an aggregate mix. The mix is then heated to a temperature of between 48°–55° C. to produce a homogenised fluid mass. (Homogenisation can be hastened by stirring). The temperature of the homogenised fluid mass is then raised to 60° C. to reduce the viscosity of the mass to a workable level. 2 mls of Jasmine perfume is then added to the fluid mass and the mix stirred for 5 minutes. The fluid mass is then allowed to cool to produce a soft wax block. (Up to 12 mls of perfume can be added, if desired, to the above homogenised fluid mass).

I claim:

1. An air freshener consisting essentially of a homogenized mixture of polyethylene glycol and water as a plasticizing agent, said mixture having a perfume incorporated therein and therethrough.

2. In the process of manufacturing air fresheners by incorporating a perfume in a solid softenable material, the improvement comprising the steps of mixing a particulate solid polyethylene glycol with a plasticizing amount of water to form a slurry, heating and agitating said slurry until said slurry is homogenized, adding a perfume to the homogenized material while agitating to disperse the perfume throughout said homogenized material and solidifying said material.

3. A process according to claim 2 comprising the step of heating the homogenized material to about 60° C. before addition of the perfume thereto.

* * * * *